United States Patent [19]

Warrin

[11] 4,051,337

[45] Sept. 27, 1977

[54] DENTAL HANDPIECE SWITCH

[75] Inventor: George E. Warrin, North Merrick, N.Y.

[73] Assignee: Cavitron Corporation, New York, N.Y.

[21] Appl. No.: 652,682

[22] Filed: Jan. 27, 1976

[51] Int. Cl.² .............................................. H01H 9/06
[52] U.S. Cl. ..................................... 200/61.85; 32/26; 32/DIG. 4
[58] Field of Search ... 200/157, 61.58 R, 61.54–61.57, 200/52 R, 85 R, 86 R, 153 LA, 60, 159; 32/DIG. 32, DIG. 4, 26

[56] References Cited

U.S. PATENT DOCUMENTS

| | | | |
|---|---|---|---|
| 1,242,115 | 10/1917 | Russell | 200/157 X |
| 2,773,148 | 12/1956 | Roby et al. | 200/86 R |
| 2,816,977 | 12/1957 | De Kramer | 200/153 LA |
| 3,075,288 | 1/1963 | Balamuth et al. | 32/58 |
| 3,076,904 | 2/1963 | Kleesattel et al. | 310/26 |
| 3,909,564 | 9/1975 | Scheingold et al. | 200/159 B |
| 3,911,241 | 10/1975 | Jarrard | 200/157 |
| 3,956,826 | 5/1976 | Perdereaux | 32/58 |

Primary Examiner—Robert K. Schaefer
Assistant Examiner—Morris Ginsburg
Attorney, Agent, or Firm—Philip Sperber

[57] ABSTRACT

A handpiece electrical switch assembly is shown comprising a pair of electrical contacts having a dielectric spacer sandwiched between the contacts, the spacer having an opening therein all mounted on the handpiece, and a sliding activator mounted on the handpiece acting to cam a cantilevered finger against the electrical contacts forcing them into electrically conductive contact with each other.

2 Claims, 4 Drawing Figures

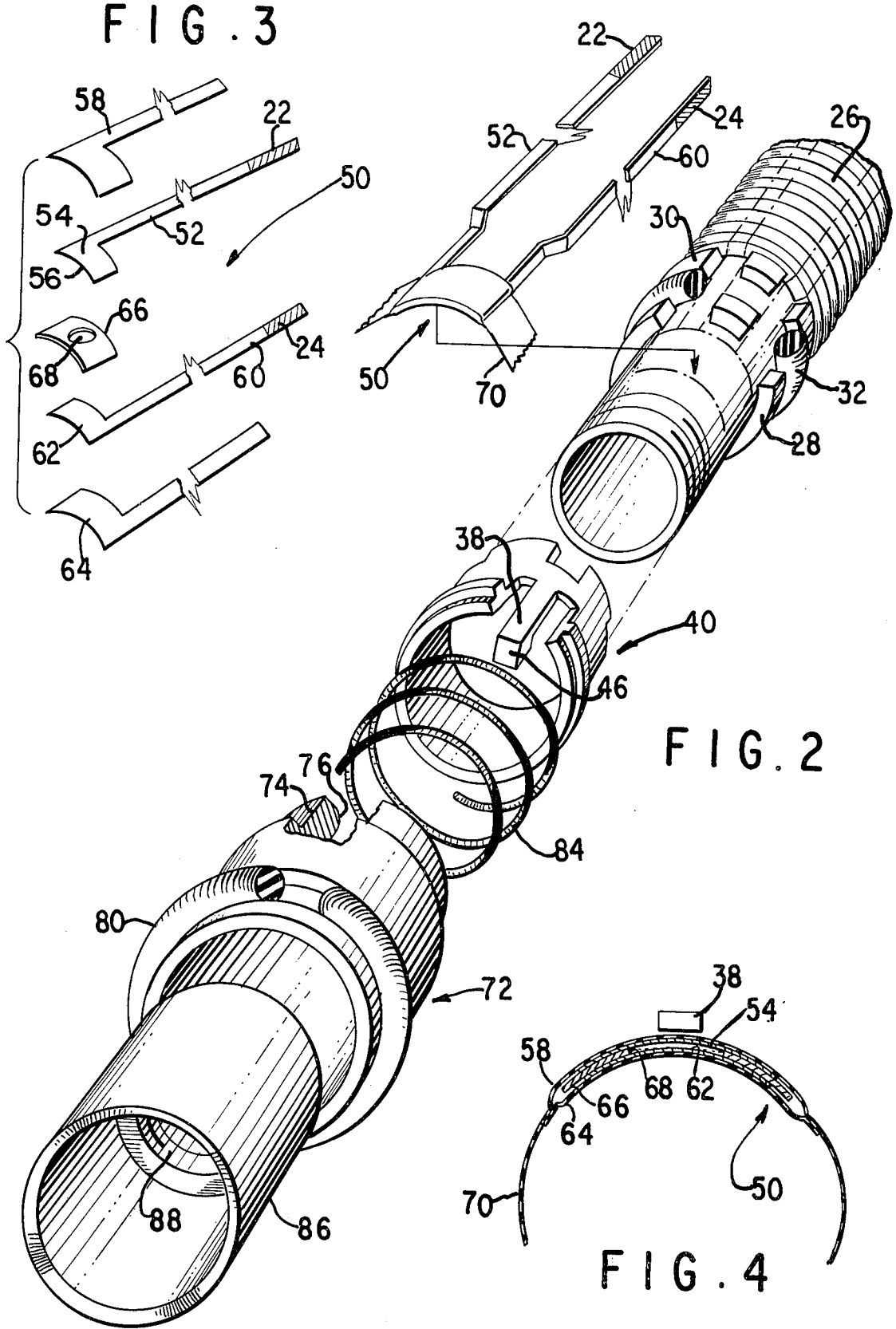

DENTAL HANDPIECE SWITCH

BACKGROUND OF THE INVENTION

This invention relates to an electrical switching device. More particularly, this invention relates to novel switching assembly mounted on a handpiece for actuating electrically the hand-held device. At present there exists a tremendous quantity of hand-held electrical powered devices of all sizes and uses, from low horsepower drills, powered toothbrushes, electrical shavers to rather large commercial drills, saws, etc. In many of these devices the on-off switch is located on the hand-held portion of the device, on a pistol grip or other convenient location. Generally the electrical switch, while custom designed for the specific device, is a variation of a conventional low power electrical switch employing either push button or toggle actuation to make or break contact points. Such switches are generally sufficiently safe, reliable and economical for such purposes and are so numerous and commonplace that they need not be further described herein.

I have invented a novel switch and hand-held assembly for use in a moist environment which has the advantages of convenient mode of operation, substantially longer life than conventional switches as well as reliability, esthetic appeal and safety. Basically, my invention comprises a flexible miniature membrane switch mounted internally of the outside casing of the device and responsive to axially applied actuation in the finger grip area of the handpiece. Such a switch and handpiece combination is particularly useful in dental ultrasonic prophylaxis units, which are employed by dentists for cleaning teeth. Such prophylaxis ultrasonic dental handpieces are commonly used by dentists and employ an ultrasonically vibrating tip to clean the teeth by "scaling" the surfaces thereof while simultaneously a spray or stream of water is directed in the vicinity of the operating tip by the unit. The vibrating tip is generally actuated by some form of electromechanical excitation within the handpiece. Generally the handpiece does not have an on-off switch mounted thereon because of its being subject to the moist or wet environment existing in and near the mouth of the patient. The on-off switch is generally present in the remotely located generator for the unit or if desired on a foot switch which directly controls the generator.

Examples of such ultrasonic dental prophylactic units are shown by U.S. Pat. No. 3,956,826 issued May 18, 1976 for Ultrasonic Device and Method and commonly assigned, U.S. Pat. No. 3,076,094 issued Feb. 5, 1963 for Acoustically Vibrated Material Cutting and Removing Devices and U.S. Pat. No. 3,075,288 issued Jan. 29, 1963 for Dental Instrument.

It is therefore an object of this invention to provide a novel handpiece switching device;

It is yet another object of this invention to provide a miniature, reliable electrical switch suitable for finger pressure actuation.

Still another object of the present invention is to provide a switching device which is substantially protected from a moist or wet environment.

Yet another object of the present invention is to provide a substantially waterproof, airtight switch.

Another object of the present invention is to provide a finger operated switch in a dental hand-held instrument, Yet another object of the present invention is to provide a reliable, rugged, readily maintained handpiece switch assembly.

Still another object of the present invention is to provide a switch utilizing a minimum of space in a tubular handpiece.

Other objects and advantages of the present invention will be apparent from the summary, brief description of the drawings and the preferred embodiment which follows.

SUMMARY OF THE INVENTION

I have invented handpiece switching apparatus for electrical switching purposes comprising in combination, electrical contact means mounted on the handpiece, the contacts being in opposing spaced relationship, and actuation means mounted on the handpiece for forcing the contact means into contacting relationship. More particularly, the electrical contact means comprises a pair of opposed thin metallic contacts spaced apart by a thin dielectric separator having an opening, and actuation means mounted on the handpiece for forcing the first and second contacts into electrically conductive contact with each other. More particularly the actuation means comprises a wedge shaped finger mounted adjacent to the first contact, a slidingly movable actuator sleeve, having an undercut cam surface opposite the wedge shaped finger for forcing the finger against the contact with sufficient force to cause electrical contact between the two contacts, and biasing means for maintaining the actuator sleeve and finger apart from each other unless a force is applied to the actuator sleeve.

With a view to further describing my invention the following is a brief description of the drawings and the preferred embodiment of the invention.

BRIEF DESCRIPTION OF THE DRAWINGS

FIG. 2 is an assembly view of the device;

FIG. 3 is a view of the partially assembled switch of the present invention; and FIG. 4 is a more detailed view of the switch elements shown in FIG. 3 taken along Section 4—4 of FIG. 1.

DESCRIPTION OF THE PREFERRED EMBODIMENT

Figure 1:
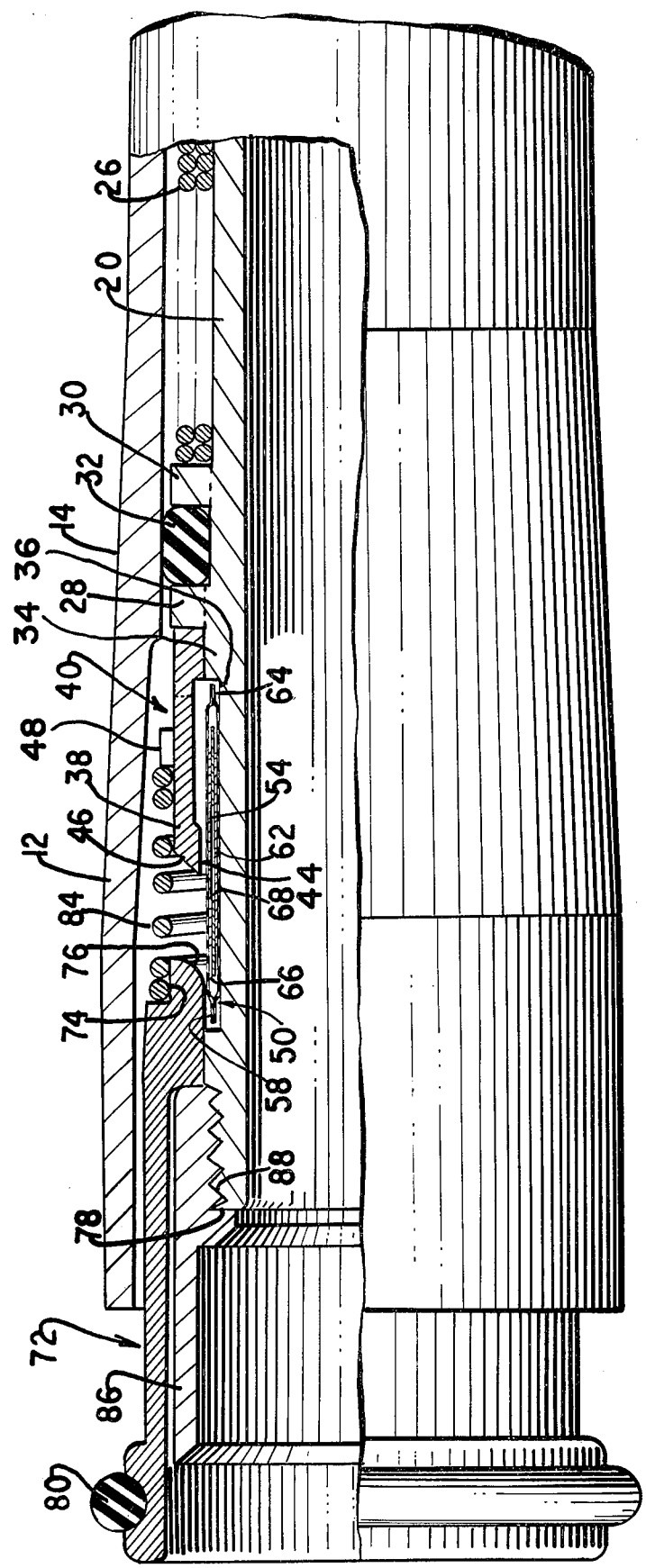
FIG. 1 is a sectional elevation of the switching device according to the present invention.

Conventional switches for ultrasonic dental prophylaxis units are normally located in the generator or in a footswitch, the latter enabling the operator, a dentist or dental technician, to switch the unit on or off as desired without having to direct either his attention or his hands from the patient. While it would have been obviously convenient to place a switch on the handpiece, the fact that the handpiece is employed in a moist or wet environment has generally precluded such a design feature due to problems of reliability, safety and shock hazard. My invention is directed to a switch and handpiece combination which overcomes the problems posed by such an environment. Such ultrasonic handpieces are usually tubular in shape and relatively convenient to hold in one hand, much as a large pencil is held. The ultrasonically vibrated tip is located at the anterior end and some form of delivery for a spray of water is also present at the anterior end. A cable enclosing the necessary electrical wires and water supply tubing connects the handpiece to its generator and water supply.

Referring now to FIG. 1 of the drawings, where the anterior half of the dental ultrasonic handpiece 12 is shown in cross-section. The handpiece 12 comprises a housing 14, generally tubular in shape which forms the greater part of the outside surface of the handpiece. Within the housing is an axially mounted hollow tubular coil form 20. Electrical wiring from a cable (not shown) is connected to two switch terminals 22 and 24 (see FIG. 2) and to a wound coil 26 wound about the coil form 20.

High frequency electrical current generated by the units power supply (not shown) passing through the wound coil 26 acts to ultrasonically vibrate a magnetostrictive stack (also not shown) and transmit such vibration to the handpieces tool tip as described in the above-mentioned U.S. patents. At the anterior end of the coil 26 two spaced apart annular rims 28 and 30 are molded as part of the coil form 20 and an elastomeric O-ring 32 is retained therebetween. The O-ring 32 acts as an elastic support and seal between the coil form 20 and the handpiece housing 14.

Immediately anterior of the rim 28 is a short annular ridge 34 and a shallow wide annular cutout 36 also on the coil ridge 34 outer surface. An elongated finger 38 extending over the cutout 36 is mounted on a sleeve retainer 40 which is positioned on the coil form ridge 34.

The projecting finger 38 has a claw extending downwardly towards the cutout with a flat tip 44 opposingly facing the surface of the cutout 36. The forward side of the claw is inclined posteriorly so as to effectively create a wedge shaped portion 46 in the fingers forward tip. An upwardly extending circumferential spring detent 48 is located on the sleeve retainer about midway of its length.

Circumferentially mounted in the space provided by the cutout 36 is the membrane switch contact assembly 50 according to the present invention.

The contact assembly 50 comprises two metal foils acting as the contacts separated by a thin flat insulator having a central opening. The foils are backed by thin plastic insulation overlapping the contact surfaces thereby forming a substantially sealed pair of electrical contacts in a rather thin flat sandwiched configuration, as illustrated in FIG. 4 of the drawings.

Referring now to FIG. 3 of the drawings, the terminals 22 and 24 are shown as being the outer end of a first leg 52 on an upper switch contact 54 formed by a flag shaped metal contact portion 56 at the other end thereof. The inner face of the contact portion 56 is preferably gold plated for corrosion free operation. A first insulated overlay 58 extends the whole length of the first leg 52 from the contact portion to the terminal end 22. The width of the overlay 58 is sufficiently wide except at the terminal portion to completely wrap around the leg and satisfactorily insulate the metal leg 52.

Terminal 24 is formed on the posterior end of a second leg 60 connected to a second contact portion 62 and a second overlay 64 which is the image of the respective previously described similarly named structure. The two contact portions 56 and 62 are positioned opposite each other with the gold plated faces of the contacts facing each other. A dielectric separator 66 is mounted in opposing contact between the two contacts. The separator is preferably a thin, (preferably 0.004 inch,) double coated polyester film with a circular opening 68 in its center. Dimensionally the separator 66 is wider and longer than the two similarly sized contacts and butts up against the two overlays on each leg. The separator where it contacts the surface of the contacts is adhesively coated and thereby forms a substantially sealed area surrounding the circular opening 68 in the separator.

The contact assembly 50 is formed into the shape shown in FIGS. 3 and 4 of the drawings by bending over the terminal portions of each of the legs, bending portions of the insulated legs to properly fit on the coil form as desired and to bend the assembled contact and separator in a semi-circular shape to fit into the space provided by the cutout 36 on the coil form. Preferably the metal legs and contact portion are made of a high ductility copper foil with the aforesaid described gold plating and suitable solder coating as desired at the terminal ends. Preferably an adhesive polyester tape is then wrapped around the contact assembly 50 and coil form 20 as shown. The tape 70 serves to hold the contact assembly 50 in place and to provide added environmental sealing therefor.

Referring again to FIGS. 1 and 2 of the drawings, attention is now directed to a movably mounted annular slide actuator 72 which is positioned at the anterior end of the handpiece 12. The posterior end of the actuator 72 has an outer diameter enabling it to move freely within the forward end of the housing 14 which tapers generally towards O-ring 32.

The inner diameter of the actuator 72 at its posterior end is somewhat larger than the coil form diameter forward of the cutout 36 and free to slide thereover. The rear portion of the actuator face is chamfered on its internal edge to form an angled cam 76 to force the finger tip 46 inwardly against the first contact when the actuator is axially forced back by the operator. The outer posterior edge of the actuator has a shoulder 74 in the form of a annular ledge. A coil spring 84 having a somewhat larger diameter than the shoulder 74 is positioned between the shoulder and the spring detent 48 and serves to bias the actuator 72. The spring is easily compressed by the normal application of finger tip pressure against the actuator.

The coil form 20 at its anterior end is externally threaded to mate with a guide bushing 86 having an internally threaded posterior portion 88 with a flange 78 abutting the forward face of the coil form. The bushing holds the actuator in the housing. For this purpose the major portion of the bushing is molded with a slightly smaller diameter than the inside diameter of the actuator enabling the actuator to freely slide over the bushing. The forward position of the actuator has a push ring 80 adapted to be easily accessible to the operators finger tips as the handpiece is held and manipulated. For instance, a rubber O-ring held in a groove on the actuator is suitable. In operation the operator will move his fingers to slide the actuator back into the handpiece in order to actuate the switch. The beveled cam 76 of the actuator on contacting the wedge shaped forward edge of the finger 38 will force the finger tip 44 down against the contact assembly 50 with sufficient force to make electrical contact, thereby controlling operation of the handpiece as desired. Removal of operator finger pressure will allow the coil spring 84 to force the actuator forward and away from the finger thereby removing the force camming the finger tip 44 against the contact assembly. Suitable circuitry may be employed to provide a desired sequence of handpiece operational modes. Further it should be understood that the contact assembly 50 is shown in FIG. 4 of the drawings may be stacked one on top of another to provide multiple switch contacts and may be generically described as a double pole switch where two such contact assemblies are so stacked.

Having fully described my invention and wishing to cover those modifications and variations which would be apparent to those skilled in the art, without departing either from the spirit or scope thereof,

I claim,

1. A dental handpiece switching apparatus for controlling an ultrasonic dental prophylaxis handpiece in which a substantial portion of the volume of the handpiece contains a magnetostrictive stack and a stack energizing coil comprising:

a thin membrane contact assembly that is retained in a generally circumferential arrangement in the outer portion of the handpiece to minimize the size of the handpiece and including (1) a first metallic foil contact mounted on a coextensive insulating backing, (2) a second metallic foil contact mounted on a coextensive insulating backing, said first and second contacts being arranged in circumferential facing relationship and (3) a thin, non-conducting separator between said contacts and having an opening therein to permit electrical communication between said first and second contacts;

actuation means for controlling the electrical communication between said first and second contacts including (1) an actuation finger attached to the handpiece and cantilevered over said contact assembly and having a free end with (a) a flat tip generally facing said assembly in proximity to the opening in said separator and (b) an end surface adjacent said tip that is inclined with respect to said assembly, (2) a slideable moveable actuator that surrounds said handpiece and is moveable to strike said inclined surface to force said tip into contact with said assembly so that electrical communication is realized between said first and second contacts and (3) biasing means in contact with said handpiece and said actuator for normally biasing said actuator away from contact with said finger.

2. The apparatus according to claim 1 wherein said insulating backing extends beyond the edges of said first and second metallic foil contacts and is formed of substantially impervious plastic film, and further wherein the backing extensions are joined to environmentally seal said membrane contact assembly.

* * * * *